United States Patent [19]
Oh

[11] Patent Number: 6,036,952
[45] Date of Patent: Mar. 14, 2000

[54] LACTIC ACID BACTERIA INHIBITING THE FORMATION OF DENTAL PLAQUE IN THE MOUTH

[76] Inventor: Jong Suk Oh, 179-34 Hwajung-dong, Seo-ku, Kwangju-City, 502-240, Rep. of Korea

[21] Appl. No.: 09/014,436

[22] Filed: Jan. 27, 1998

[30] Foreign Application Priority Data

Aug. 7, 1997 [KR] Rep. of Korea ................. 97-37819

[51] Int. Cl.⁷ ............................ A01N 63/00; C12N 1/12; C12N 1/20
[52] U.S. Cl. ................. 424/93.1; 424/93.45; 424/93.4; 514/835; 435/252.1; 435/252.9
[58] Field of Search .................. 424/93.1, 93.45, 424/93.44; 435/252.9, 252.1; 436/20, 22, 21, 23; 426/106

[56] References Cited

U.S. PATENT DOCUMENTS

| | | | |
|---|---|---|---|
| 3,879,545 | 4/1975 | Gaffar et al. | 424/92 |
| 3,929,579 | 12/1975 | Yoshimura et al. | 195/62 |
| 4,133,875 | 1/1979 | Hill | 424/93 |
| 4,746,512 | 5/1988 | Kawai et al. | 424/92 |
| 5,135,739 | 8/1992 | Tsurumizu et al. | 424/50 |
| 5,225,344 | 7/1993 | Tsurumizu et al. | 435/353.4 |
| 5,306,639 | 4/1994 | Matsushiro | 435/320.1 |
| 5,468,479 | 11/1995 | Matsushiro | 424/93.44 |
| 5,874,613 | 2/1999 | Nikaido et al. | 562/445 |

FOREIGN PATENT DOCUMENTS 54-062364  5/1979  Japan .

OTHER PUBLICATIONS

Hamada et al. (1975) Effect of Dextranase on the Extracellular Polysaccharide Synthesis of Streptococcus mutans: Chemical and Scanning Electron Microscopy Studies, Infection and Immunity, vol. 12, pp 1415–1425.

Staat et al. (1982) In vivo Relationships of the Dextran–Degrading Oral Microbiota to Streptococcus mutans and Caries Experience, Caries Res. 16: 18–25 (1982).

Geis et al., Potential of Lactic Streptococci to Produce Bacteriocin, Applied and Environmental Microbiology, 1983, pp 205–211.

Harper et al., Clinical Efficacy of a Dentifrice and Oral Rinse Containing Sanguinaria Extract and Zinc Chloride During 6 months of Use, J. Periodontol, 1990, pp 352–358.

P.D. Marsh, Antimicrobial Strategies in the Prevention of Dental Caries, Caries Research 1993; 27 (suppl 1): 72–76.

Van der Hoeven et al, Streptococci and Actinomyces Inhibit Regrowth of Streptococcus mutans on Gnotobiotic Rat Molar Teeth after Chlorhexidine Varnish Treatment, Caries Res 1995;29:159–162.

*Primary Examiner*—James C. Housel
*Assistant Examiner*—S. Devi
*Attorney, Agent, or Firm*—Darby & Darby

[57] ABSTRACT

Enterococcus spp. 1357, *Lactobacillus acidophilus* V20 and *Lactococcus lactis* 1370, lactic acid bacterial strains having a potent and lasting inhibitory activity against the formation of glucan and dental plaque in human mouths.

2 Claims, 5 Drawing Sheets

A      B"      C"

A      B'      C'

A  B  C

A  B"

A  B

A  B

LACTIC ACID BACTERIA INHIBITING THE FORMATION OF DENTAL PLAQUE IN THE MOUTH

This application claims priority to the Korean Patent Application No. 97-37819 filed Aug. 7, 1997.

BACKGROUND OF THE INVENTION

1. Field of the Invention

The present invention relates to novel bacteria which inhibit the formation of dental plaque in human mouths. More particularly, the present invention relates to novel lactic acid bacteria capable of inhibiting the formation of glucan, a major component of dental plaque, in human mouths, which is produced from the microorganisms which normally inhabit in human mouths. These lactic acid bacteria are of the genera Enterococcus, Lactobacillus, and Lactococcus, and Lactococcus spp. which are thought to inhibit the activity of glucosyltransferase or to antagonize against the bacteria which play a role in forming glucan.

2. Description of the Prior Art

Lactic acid bacteria are those which ferment carbohydrates to produce lactic acid as a final product. Lactic acid bacteria live in the oral cavities and the alimentary tracts of men and animals and are utilized for the manufacture of fermentative foods, such as kimchi, yogurt, etc. In addition, they are reported to be used to produce biologically active materials, such as medicines. Among the lactic bacteria are those of the genera Streptococcus, Enterococcus, Lactococcus, Lactobacillus, and Bifidobacterium. Representative examples of these lactic acid-producing bacteria include *Streptococcus thermophilus, Enterococcus faecalis, Enterococcus durans, Lactococcus lactis, Lactobacillus lactis, Lactobacillus acidophilus, Lactobacillus bulgaricus, Lactobacillus thermophilus, Lactobacillus casei* and *Lactobacillus plantarum*. As inhabitants in the entrails of men and animals, these lactic acid bacteria, Gram-positive bacteria, are known to play an important role in maintaining the entrails healthy condition by utilizing carbohydrates as energy source to produce lactic acid and antibacterial materials which inhibit the growth of the harmful bacteria.

In the past, enzymes which decomposed glucan, the major component of dental plaque, were isolated to be useful for the sanitization of oral cavity. For example, dextranase ($\alpha$-1,6 glucan hydrolase) which used dextran as a substrate was purified and applied to animals and men (Staat, R. H. and Schachtete, C. F., 1975; Kaster, A. G. and Brown, L. R., 1983). In addition, it was reported that mutanase (endo-$\alpha$-1,3-glucanase) which decomposed mutan, an important component for the formation of glucan, was isolated and purified and had an inhibitory effect on the formation of dental plaque (Guggenheim B., et al., 1972; Takehara et al., 1981). However, these inhibitory enzymes against glucan formation were found to have an insignificant effect in human oral cavities. For mutanase, the decomposition effect of dental plaque is trivial and it takes a long time to express its effect. In addition, since tremendous effort and time are required for the isolation and purification of the enzyme, it is problematic in the economical and practical aspects.

SUMMARY OF THE INVENTION

As a consequence of intensive and thorough research for the inhibitory effect against glucan or dental plaque formation, the present invention is based on the finding that some lactic acid bacteria which inhabit human mouth are able to remarkably inhibit the formation of dental plaque. But the other usual lactic acid bacteria except three novel strains of the invention cannot inhibit the formation of glucan or dental plaque. Through many clinical experiments, three lactic acid-producing strains were isolated which had a great ability to inhibit the formation of dental plaque and they were named *Enterococcus durans* 1357, *Lactobacillus acidophilus* V20, and *Lactococcus lactis* 1370, respectively, which were deposited in the Korean Collection for Type Cultures, Korean Research Institute of Bioscience and Biotechnology, on 30, Jul. and 11, Dec. 1997 (deposition No. KCTC 0360BP for *Enterococcus durans* 1357, KCTC 0361BP for *Lactobacillus acidophilus* V20, KCTC 0415BP for *Lactococcus lactis* 1370).

The dental plaque in human oral cavity consists mainly of glucan, a composite of carbohydrates. Glucan is either dextran, water-soluble, or mutan, water-insoluble. Glucan is synthesized from sucrose by the glucosyltransferase secreted from *Streptococcus mutans*. Mutan has $\alpha$-1,3 linkages so that it is insoluble in water, and makes the main matrix of the dental plaque.

Generally, dental plaque, adherent to the surface of teeth, provides a suitable habitat at which *Streptococcus mutans* as well as other bacteria proliferate, and cause dental caries because food residues cling to it.

Therefore, it is an object of the present invention to provide novel bacteria which has an inhibitory effect on the formation of glucan and thus dental plaque in the mouth.

It is another object of the present invention to provide foods or beverages employing the lactic acid bacteria. That is, when the foods containing the lactic acid bacteria capable of directly inhibiting the formation of glucan or being active against the microorganisms which contribute to the formation of dental plaque, are eaten, the lactic acid bacteria suppress the formation of dental plaque and further prevent dental caries.

BRIEF DESCRIPTION OF THE DRAWINGS

Above and other objects and aspects of the invention will become apparent from the following description of embodiments with reference to the accompanying drawings in which.

DETAILED DESCRIPTION OF THE INVENTION

Figure 1A:
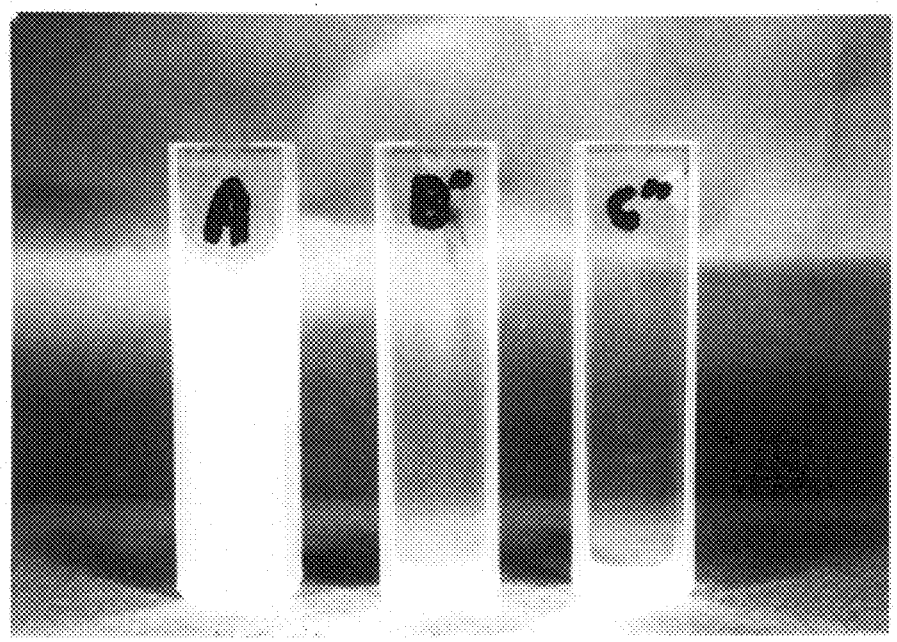
FIGS. 1a, 1b and 1c are photographs showing the inhibitory effect of the novel strains of the invention on the formation of water-insoluble glucan in a disposable cuvette.

Lactic acid bacteria were taken from human bodies, streaked on brain heart infusion agar, and cultured at 37° C. Thereafter, separated bacterial colonies were tested whether they could suppress the formation of the water-insoluble glucan that *Streptococcus mutans* produced. In a cuvette, 3 ml of a brain heart infusion medium supplemented with 0.5% yeast extract and 5% sucrose was inoculated with 0.1 ml of *Streptococcus mutans* and 0.1 ml of a culture broth of the separated bacteria. As a control, *Streptococcus mutans* was inoculated alone in a brain heart infusion medium containing yeast extract and sucrose. The cuvette was placed at an angle of 30° to the horizontal surface of an incubator and incubated for 1 day at 37° C., in order for the *Streptococcus mutans* to produce water-insoluble glucan. After removal of the broth, the cuvette was washed with 4 ml of distilled water and then, filled with 3 ml of distilled water. Its absorbance (OD) at 550 nm was measured by a spectrophotometer. Because the OD value was proportional to the glucan produced, the bacteria which brought about a significantly lower OD value compared with the control, were isolated as dental plaque-inhibitory strains.

The microbiological properties, such as morphological and physiological properties, and sugar catabolytic ability of the isolated strains were investigated. Table 1 shows the morphological and physiological properties and Table 2 shows the catalytic ability for sugars.

TABLE 1

Morphological and Physiological properties

| Properties | Isolated Bacterial Strains | | |
|---|---|---|---|
| | Enterococcus durans 1357 | Lactobacillus acidophilus V20 | Lactococcus lactis 1370 |
| Size | 0.5–1 μm | 0.6–0.9 × 2–6 μm | 0.5–1 μm |
| Morphology | coccus, chain | bacillus, chain | coccus, chain |
| Gram stain | positive | positive | positive |
| Spore forming | − | − | − |
| Catalase Activity | − | − | − |
| Culture Temp. 10° C. | + | − | + |
| Culture Temp. 45° C. | + | + | − |
| pH 9.6 | + | − | − |
| 40% bile acid | + | − | + |
| 6.5% NaCl | + | − | − |
| Growth on MRS medium | − | + | − |
| Acetoin Production | + | − | + |
| Hippurate Hydrolysis | + | − | − |
| Pyrrolidonylary amidase | + | − | − |
| α-Galactosidase | − | − | − |
| β-Glucuronidase | − | − | − |
| β-Galactosidase | + | − | − |
| Alkaline phosphatase | − | − | − |
| Leucine arylamidase | + | − | + |
| Arginine dihydrolase | + | − | − |

TABLE 2

Catalytic Activity for Sugars

| Carbohydrate | Enterococcus durans 1357 | Lactobacillus acidophilus V20 | Lactococcus lactis 1370 |
|---|---|---|---|
| Arabinose | − | − | − |
| Amygdalin | + | − | − |
| Cellobiose | + | + | + |
| Esculin | + | + | − |
| Fructose | + | + | + |
| Galactose | + | + | + |
| Glucose | + | + | + |
| Lactose | + | + | + |
| Maltose | + | + | + |
| Mannitol | − | − | + |
| Mannose | + | + | + |
| Melezitose | − | − | − |
| Raffinose | − | − | − |
| Rhamnose | − | − | − |
| Salicin | + | − | − |
| Sorbitol | − | − | − |
| Trehalose | + | + | + |
| Inulin | − | − | − |
| Starch | + | − | + |
| Glycogen | − | − | − |

As mentioned above, the novel lactic acid bacteria capable of inhibiting the formation of dental plaque were isolated and assayed in comparison with the control in vitro. Further, the invention was tested in vivo, that is, the isolated bacteria were applied to the human oral cavity.

A better understanding of the present invention may be obtained through the following examples which are set forth to illustrate, but are not to be construed as the limit of the present invention.

EXAMPLE I

Inhibition of the Formation of Water-Insoluble Glucan in Disposable Cuvette

Figure 1B:
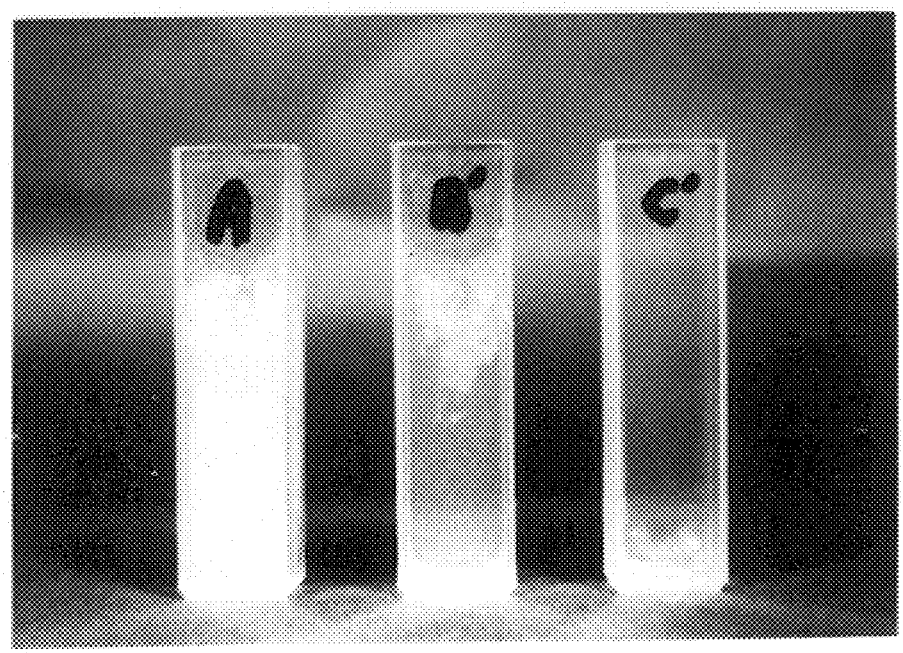
Figure 1C:
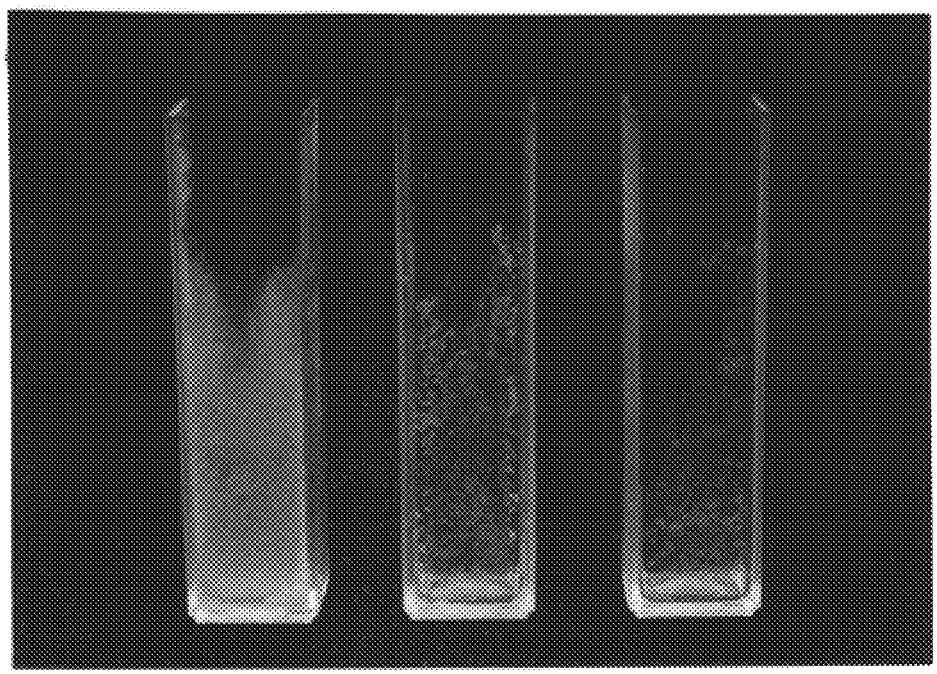

An equal amount of M17 medium was mixed with MRS medium and supplemented with 0.5% yeast extract and 5% sucrose. Three milliliters of the constituted medium were transferred to a disposable cuvette which was, then, inoculated with 75 μl of a *Streptococcus mutans* overnight culture. The cuvette was placed at an angle of 30° C. to the horizontal side in an incubator and cultured at 37° C. for 1 day. The content was removed and then, the cuvette was washed with 3 ml of distilled water. Pictures were taken of the cuvette (FIGS. 1a, 1b and 1c). Thereafter, the cuvette was filled with 4 ml of distilled water and the absorbance at 550 nm was measued by a spectrophotometer. This measurement was repeated three times and an average value was obtained (Table 3).

FIGS. 1a(A), 1b(A) and 1c(A) are the photographs of the control cuvette in which *Streptococcus mutans* is cultured alone and FIG. 1a(B") is obtained when *Streptococcus mutans* and *Enterococcus durans* 1357 at the concentration of 5 times higher than that of *Streptococcus mutans* are co-cultured, and FIG. 1a(C") when *Enterococcus durans* 1357 is cultured alone. FIG. 1b(B') is a photograph taken of the cuvette in which *Streptococcus mutans* and *Lactobacillus acidophilus* V20 at the concentration of 5 times higher than that of *Streptococcus mutans* are co-cultured and FIG. 1b(C') shows the cuvette in which *Lactobacillus acidophilus* V20 is cultured alone. FIG. 1c(B) is a photograph taken of the cuvette in which *Streptococcus mutans* and *Lactococcus lactis* 1370 at the concentration of 5 times higher than that of *Streptococcus mutans* are co-cultured and FIG. 1c(C) shows the cuvette in which *Lactococcus lactis* 1370 is cultured alone.

TABLE 3

Inhibitory Effect against Glucan Formation

| Samples | Lactic acid bacterial strains inoculated | OD 550 nm |
|---|---|---|
| 3-A | | |
| Control | Streptococcus mutans | 2.122 |
| Group I | Enterococcus durans 1357 | 0.434 |
| Group II | Enterococcus durans 1357 + Streptococcus mutans | 0.713 |
| Group III | Lactobacillus acidophilus V20 | 0.506 |
| Group IV | Lactobacillus acidophilus V20 + Streptococcus mutans | 1.154 |
| 3-B | | |
| Control | Streptococcus mutans | 1.765 |
| Group V | Lactococcus lactis 1370 | 0.479 |
| Group VI | Lactococcus lactis 1370 + Streptococcus mutans | 0.848 |

As given in Table 3-A, the control (*Streptococcus mutans* alone) is 2.122 in absorbance whereas Test group II (co-inoculated with *Enterococcus durans* 1357) and Test group IV (co-inoculated with *Lactobacillus acidophilus* V20) are 0.713 and 1.154 in absorbance, respectively. This reduction in the absorbance means that *Enterococcus durans* 1357 and *Lactobacillus acidophilus* V20 each inhibit the *Streptococcus mutans*' forming of glucan. In addition, Test group I (inoculated with *Enterococcus durans* 1357 alone) and Test group III (inoculated with *Lactobacillus acidophilus* V20 alone) show 0.434 and 0.506 in absorbance at 550 nm, respectively. As given in Table 3-B, the control (*Streptococcus mutans* alone) is 1.765 in absorbance whereas Test group V (inoculated with *Lactococcus lactis* 1370 alone) and Test group VI (co-inoculated with *Streptococcus mutans* and Lactococcus spp. 1370) are 0.479 and 0.848 in absorbance, respectively. This reduction in the absorbance means that *Lactococcus lactis* 1370 inhibits the *Streptococcus mutans*' forming of glucan, too.

EXAMPLE II

Artificial Dental Plaque Formation on Orthodontic Wire

Figure 2A:
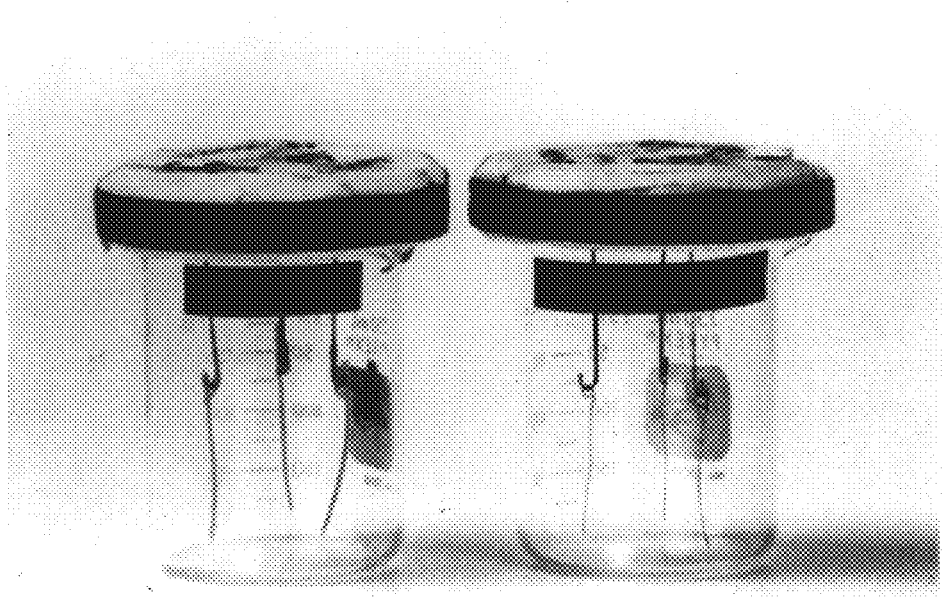
FIGS. 2a, 2b and 2c are photographs showing the inhibitory effect of the novel strains of the invention on the formation of artificial dental plaque on an orthodontic wire.
Figure 2B:
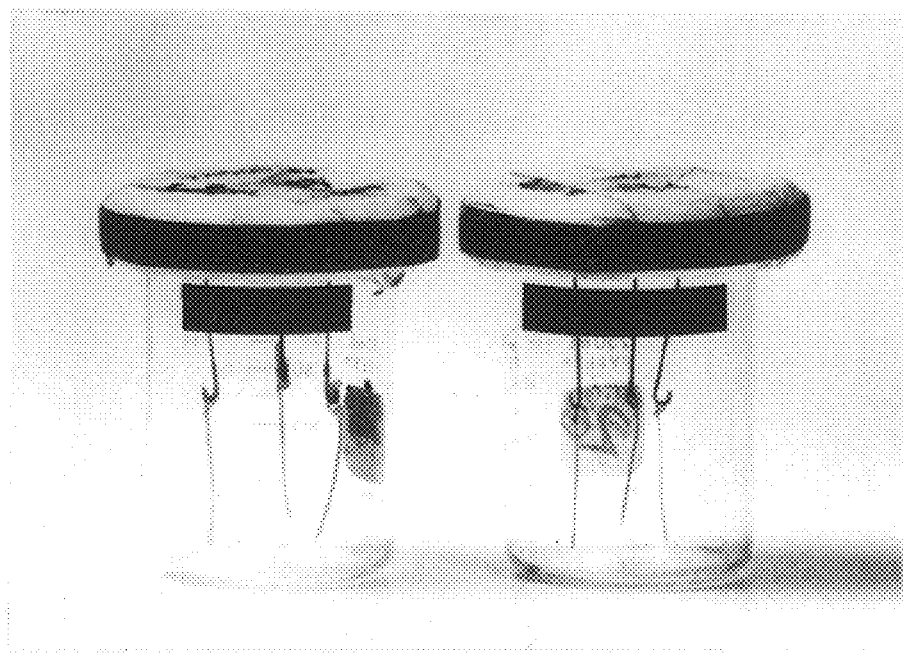
Figure 2C:
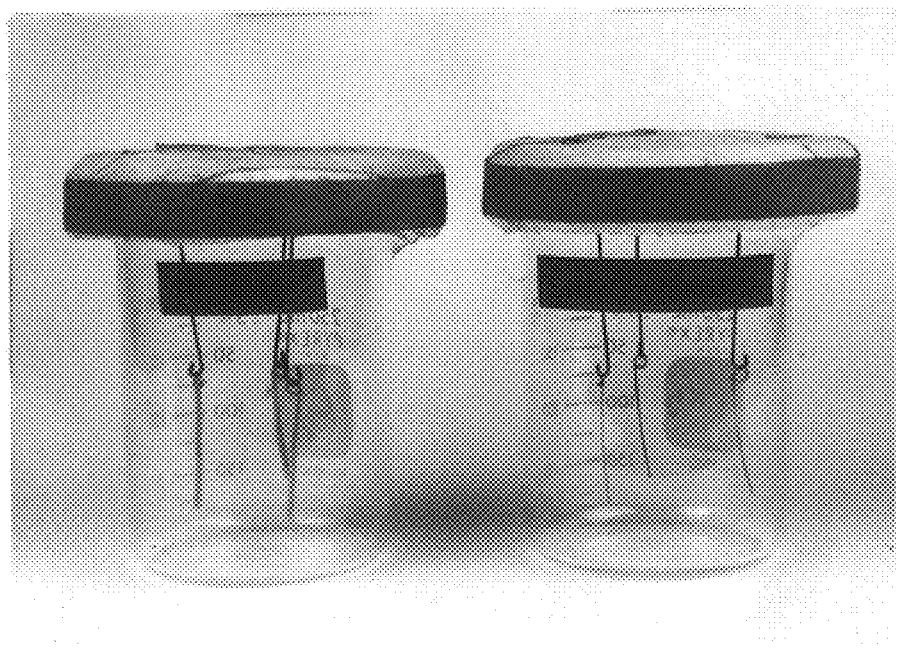

An equal amount of M17 medium was mixed with MRS medium and supplemented with 0.5% yeast extract and 5% sucrose. One hundred and fifty milliliters of the consitituted medium were poured into a beaker. 0.016 inch stainless steel orthodontic wires (45 mg) were immersed in the medium. *Streptococcus mutans* was inoculated at the concentration of $2.5 \times 10^6$ per ml of the medium. Thereafter, the lactic acid bacterial strains were inoculated in the medium at the concentration of 5 times higher than that of *Streptococcus mutans* and incubated in a $CO_2$ incubator at 37° C. for 6.5 hours with shaking. The wires were transferred to fresh beakers and photographed (FIGS. 2a, 2b and 2c). FIGS. 2a(A), 2b(A) and 2c(A) are photographs of the culture of *Streptococcus mutans* alone while FIG. 2a(B") is that of the co-culture of *Streptococcus mutans* and *Enterococcus durans* 1357, FIG. 2b(B) is that of the co-culture of *Streptococcus mutans* and *Lactobacillus acidophilus* V20, and FIG. 2c(B) is that of the co-culture of *Streptococcus mutans* and *Lactococcus lactis* 1370.

The weights of the artificial plaques formed on the wires were measured and the results are given in Table 4 below.

TABLE 4

Inhibitory Effect against the Formation of Artificial Plaque

| Samples | Lactic acid bacterial strains | Weight of produced plaque |
|---|---|---|
| Control | Streptococcus mutans | 75.4 mg |
| Group I | Enterococcus durans 1357 + Streptococcus mutans | 0.0 mg |
| Group II | Lactobacillus acidophilus V20 + Streptococcus mutans | 30.9 mg |
| Group III | Lactococcus lactis 1370 + Streptococcus mutans | 0.0 mg |

The control group in which *Streptococcus mutans* was inoculated alone formed an artificial plaque of 75.4 mg while no artificial plaque was formed on Test group I in which *Enterococcus durans* 1357 was co-cultured with *Streptococcus mutans*, and Test group III in which *Lactococcus lactis* 1370 was co-cultured with *Streptococcus mutans*. In the Test group II in which *Lactobacillus acidophilus* V20 was co-cultured with *Streptococcus mutans*, the plaque weight was reduced to 30.9 mg. Consequently, these data show that the novel lactic acid bacterial strains of the invention, *Enterococcus durans* 1357, *Lactobacillus acidophilus* V20 and *Lactococcus lactis* 1370, have a potent inhibitory effect against the formation of dental plaque.

EXAMPLE III

Inhibition of the Dental Plaque Formation in Human Mouth

In order to measure the inhibitory potency of the novel lactic acid bacterial strains against the formation of dental plaque in human mouths, experiments were performed in a normal healthy adult over a regular period.

Figure 3A:
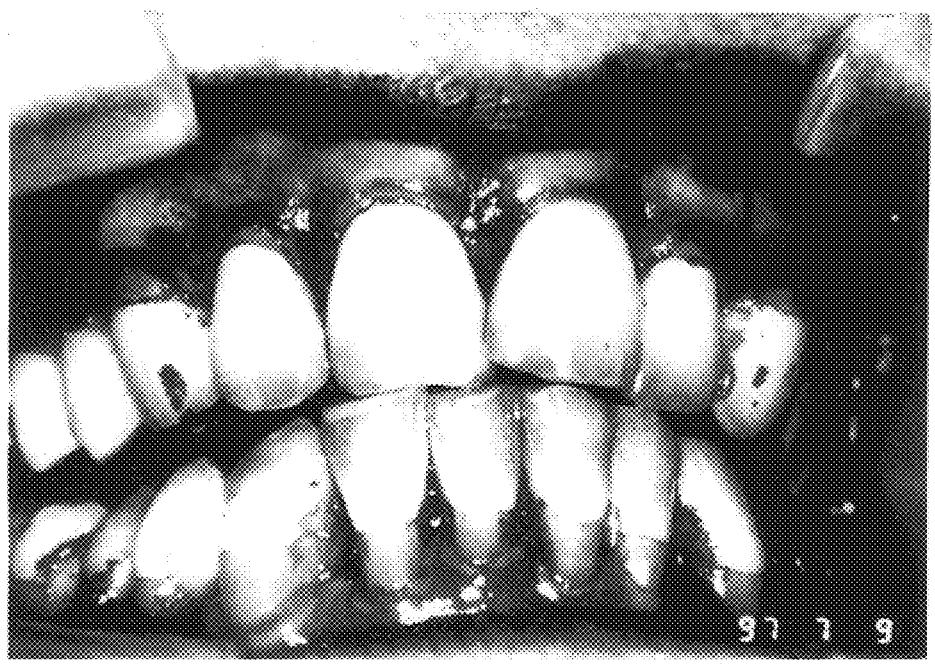
FIGS. 3a to 3c are photographs showing the inhibitory effect of the novel strains of the invention on the formation of dental plaque in oral cavity.
Figure 3B:
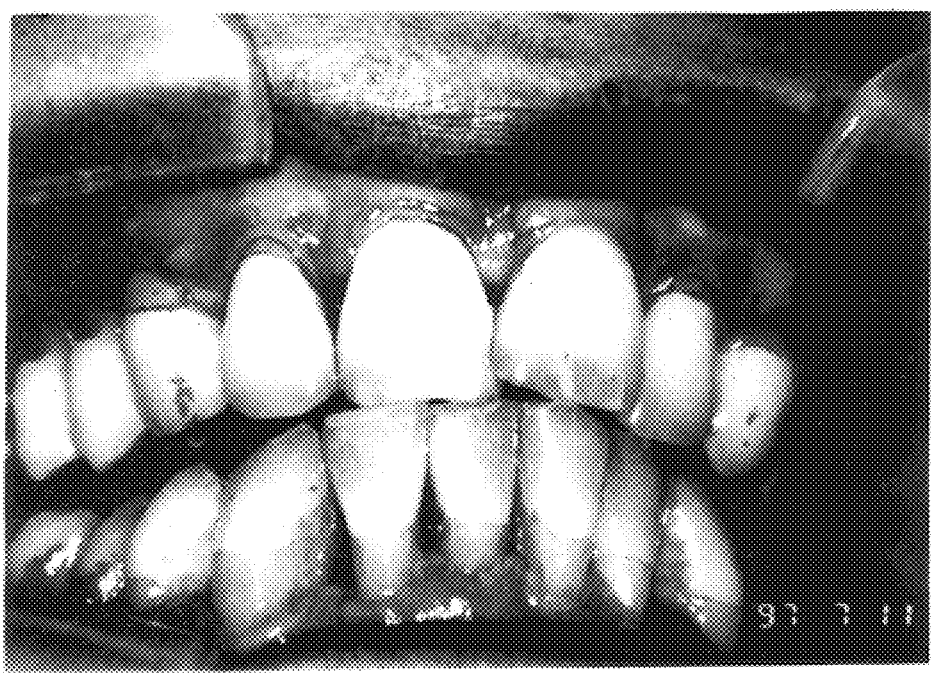

Six hours after brushing his teeth, his teeth were applied with a disclosing solution, a staining solution for dental plaque, and washed with water (FIG. 3a). Two days later, the person had his teeth brushed and he drank 50 ml of a *Enterococcus durans* 1357 culture in a skim milk solution. After 6 hours, his teeth were applied with the disclosing solution and washed with water and a photograph was taken (FIG. 3b).

Figure 3C:

After 13 days, the person had his teeth brushed and he drank 50 ml of a *Lactobacillus acidophilus* V20 culture in skim milk. Six hours later, the teeth were applied with the disclosing solution and washed with water and a photograph was taken of (FIG. 3c).

As shown in FIG. 3a, a significant amount of dental plaque was formed on the teeth and gingival cervix. When the lactic acid beverage containing the novel strain of the invention was drunk, a significant inhibitory effect against dental plaque formation was obtained as shown in FIGS. 3b and 3c.

EXAMPLE IV

Reduction of the Dental Plaque Index in Human Mouths

In order to evaluate the reduction effect of the novel lactic acid bacterial strains on plaque index in human mouths, experiments were performed in thirty-eight persons to achieve the plaque scores by Quigley and Hein Plaque Index.

Thirty-eight young adults, 22 to 26 years of age, volunteered to participate for this study. All volunteers received thorough oral prophylaxis, and all their oral hygenic activities were suspended. Volunteers ate and drank as usual, but stopped brushing their teeth. Baseline plaque scores were assessed at 24 hours after recieving oral prophylaxis. Plaque scores were performed by Quigley and Hein Plaque Index after disclosing all plaque except third molars. The volunteers were randomly assigned to two groups (each nineteen persons), the group mouthrinsing with *Lactococcus lactis* 1370 and the group mouthrinsing with *Lactobacillus acidophilus* V20. Test suspensions were prepared by incubating *Lactococcus lactis* 1370 and *Lactobacillus acidophilus* V20 in milk for 24 hours. Volunteers rinsed immediately once after oral prophylaxis and twice after meals with 20 ml of *Lactococcus lactis* 1370 or *Lactobacillus acidophilus* V20 culture in milk ($10^9$ CFU/ml) for 2 minutes. Plaque scores were again assessed at 24 hours after recieving oral prophylaxis. The plaque scores of total teeth except third molars were averaged and statistically analysed in each group. The results indicated that plaque index reduction of 0.97 in the group mouthrinsing with *Lactococcus lactis* 1370 and 0.55 in the group mouthrinsing with *Lactobacillus acidophilus* V20 at 24 hours after recieving oral prophylaxis (Table 5). The reductions of plaque index were statistically significant ($p<0.05$). *Lactococcus lactis* 1370 and *Lactobacillus acidophilus* V20 reduce plaque formation in the oral cavity.

TABLE 5

Reduction of the Plaque Index by Bacterial Mouthrinse.

| Used Bacteria | Mean Baseline Plaque Score | Mean Plaque Score after Bacterial Mouthrinse | Difference |
| --- | --- | --- | --- |
| Lactococcus lactis 1307 | 2.17 | 1.20 | −0.97* |
| Lactobacillus acidophilus V20 | 2.15 | 1.60 | −0.55* |

*$p < 0.01$ by paired t test

Hereinafter, there are given examples in which the lactic acid bacterial strains of the invention can be applied.

EXAMPLE I: Yogurt

A broth culture containing the lactic acid bacterial strains of the invention was added at an amount of 0.1 vol. percent to the food just before fermentation and subjected to fermentation along with the existing bacteria, to produce yogurt. The resulting yogurt were tasted by 10 panelists. They noted no different flavor between the test samples and the commercially available foods (controls).

Before a sealing step in the manufacture procedure, the lactic acid bacterial strains of the invention were added at an amount of 0.2 vol. percent. A response that these test samples thus obtained were not different from the control foods in taste, was drawn from 10 panelists who took part in the tasting tests.

EXAMPLE II: Kimchi

Five heads of cabbage were cut into fragments 4–5 cm long, pickled with salt and washed with water. The pickled cabbage was mixed together with condiment and aged for 3 days at 20° C. To this kimchi, broth cultures of *Enterococcus durans* 1357, *Lactobacillus acidophilus* V20 and *Lactococcus lactis* 1370 each were added at an amount of 0.2 wt percent. Ten panelists who tasted both the samples and the controls replied that there was no taste difference between them.

EXAMPLE III: Butter

Before a packaging step, butter which were manufactured by a typical procedure were added with 0.2 wt. percent of the freeze-dried lactic acid bacterial strains of the invention. These butter thus obtained were given as taste samples.

EXAMPLE IV: Cheese

Before a packaging step, cheese which were manufactured in a typical procedure were added with 0.2 wt. percent of the freeze-dried lactic acid bacterial strains of the invention. These cheese thus obtained were given as taste samples.

Additionally, the lactic acid bacterial strains of the invention were applied for various foods, including gum, shortening, ice cream, margarine, etc, which were not restrictive but illustrative.

From the examples above, it is apparent that the novel lactic acid strains of the invention have a potent and lasting inhibitory effect against the formation of dental plaque in human mouths and are very useful in the dental medicine industry.

In addition, the novel strains of the invention were found to be able to be applied for various foods as well as directly to the teeth.

The present invention has been described in an illustrative manner, and it is to be understood the terminology used is intended to be in the nature of description rather than of limitation.

Many modifications and variations of the present invention are possible in light of the above techniques. Therefore, it is to be understood that within the scope of the appended claims, the invention may be practiced otherwise than as specifically described.

What is claimed is:

1. Isolated lactic acid bacterium of the genus Lactococcus having an inhibitory activity against the formation of glucan or dental plaque in human mouths, said isolated lactic acid bacterium having the identifying characteristic of *Lactococcus lactis* 1370.

2. Isolated lactic acid bacterium of the genus Lactococcus which produces a statistically significant reduction in a plaque index in a 24 hour period of exposure in human mouths, wherein said lactic acid bacterium is *Lactococcus lactis* 1370.

* * * * *